United States Patent [19]

Gee, Sr.

[11] 3,958,690

[45] May 25, 1976

[54] MEDICAL INFORMATION AND MEDICATION PACKAGE

[76] Inventor: Robert W. Gee, Sr., 18309 Faysmith Ave., Torrance, Calif. 90504

[22] Filed: Nov. 1, 1974

[21] Appl. No.: 520,019

[52] U.S. Cl................................. 206/232; 150/35; 206/534; 206/38
[51] Int. Cl.²................. B65D 85/56; B65D 83/04; A45C 15/00
[58] Field of Search ........... 206/232, 534, 531, 532, 206/539, 39, 37, 38; 229/11, 19; 150/34, 35

[56] References Cited
UNITED STATES PATENTS

| | | | |
|---|---|---|---|
| 3,076,541 | 2/1963 | Volckening | 206/232 |
| 3,117,608 | 1/1964 | Goss et al. | 206/39 |
| 3,305,077 | 2/1967 | Greif et al. | 206/232 |
| 3,402,808 | 9/1968 | Yannuzzi | 206/232 |
| 3,504,788 | 4/1970 | Gray | 206/531 |
| 3,677,397 | 7/1972 | Beckham | 229/11 |

*Primary Examiner*—William T. Dixson, Jr.
*Attorney, Agent, or Firm*—William H. Pavitt, Jr.

[57] ABSTRACT

A medical identification, information and emergency medication packet adapted for wearing or carrying by a patient, said packet comprising an envelop—preferably transparent; a foldable information card slidably insertable in said envelope; and a frame comprehended within the card when so folded; said frame with the inside of the folded card defining at least one space within which is housed a dosage quantity of a medication to be administered to the patient in an emergency in accordance with instructions printed on said card.

6 Claims, 7 Drawing Figures

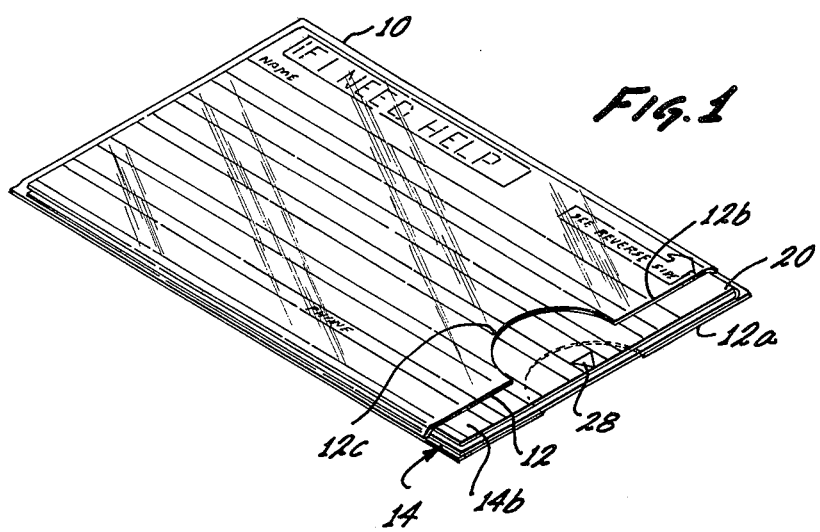
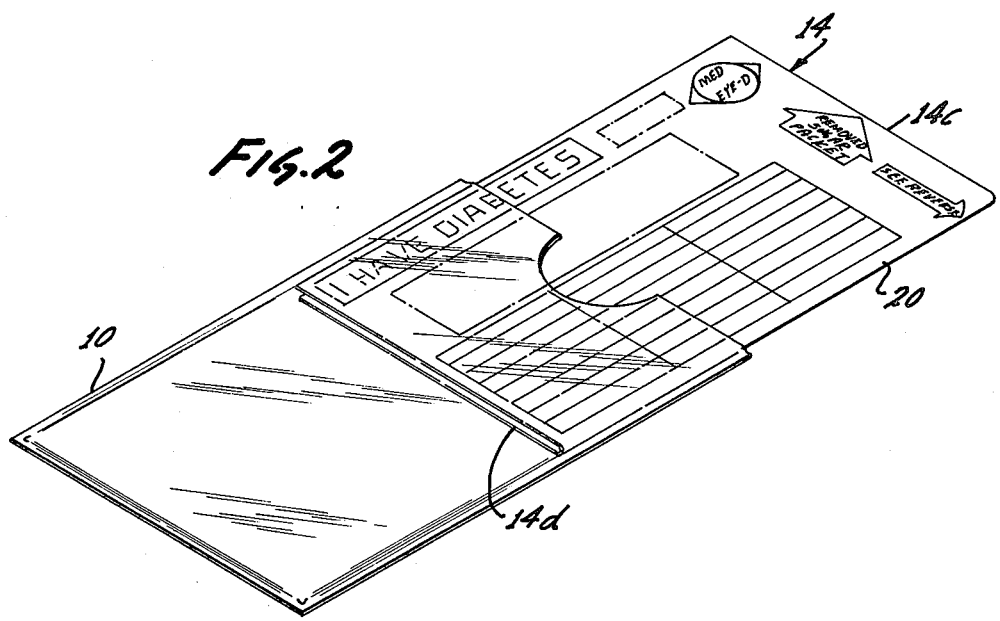
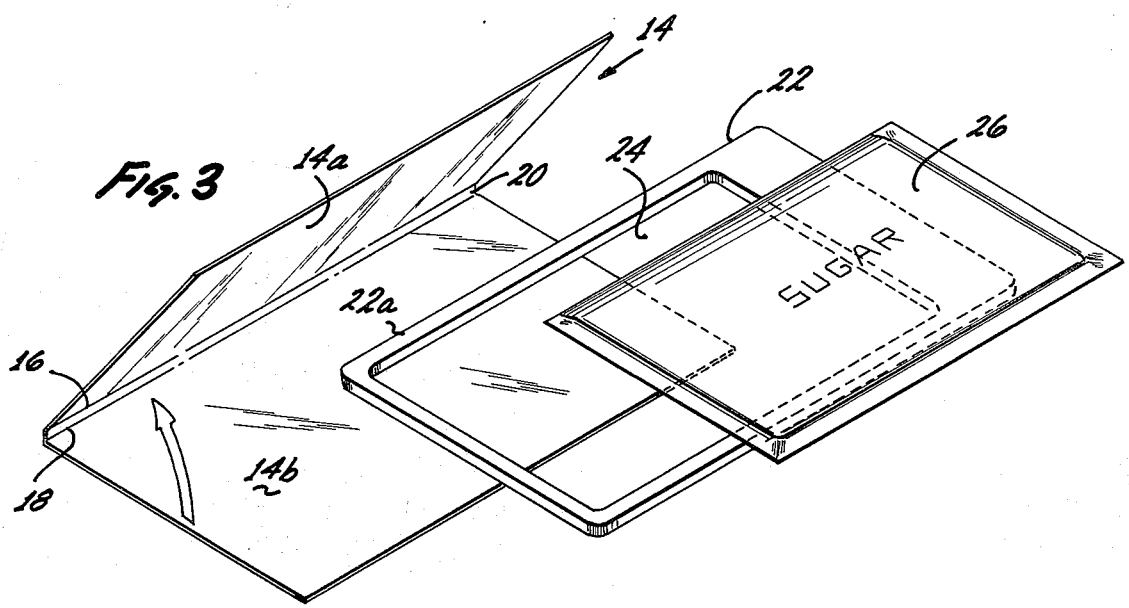

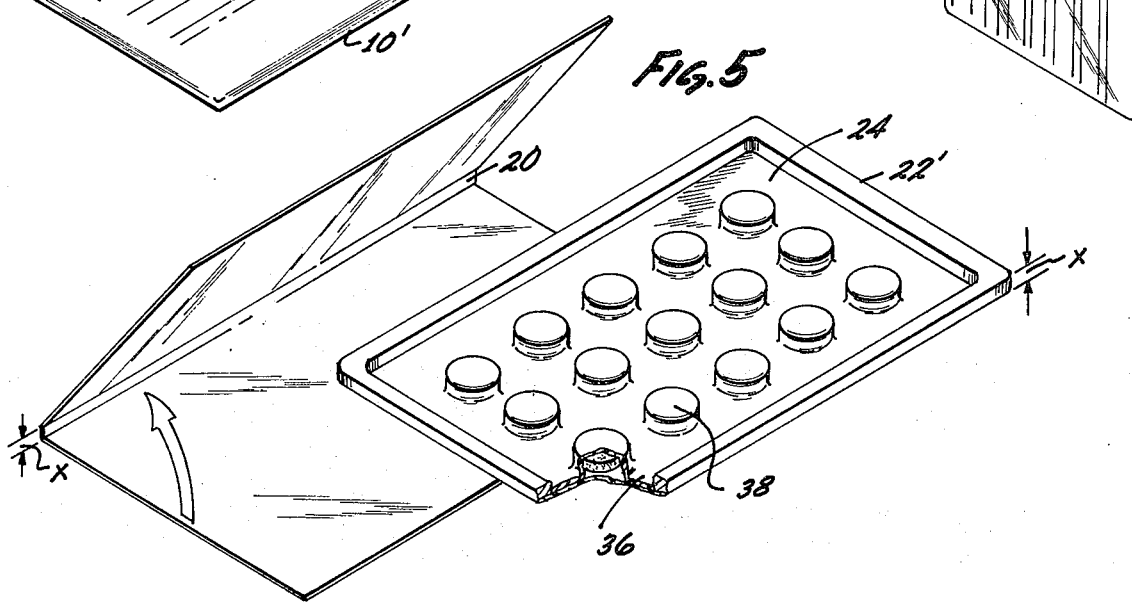

MEDICAL INFORMATION AND MEDICATION PACKAGE

BACKGROUND OF THE INVENTION

A. Field of the Invention

This invention relates generally to the field of medicine, and specifically to that area of medicine involving providing identification and medical information together with a dose of a medication for emergency use by or for a patient.

B. Description of the Prior Art

Almost as far back in history since medications have been manufactured in tablet form, various flat packages have been devised to contain them. Thus, the 1877 U.S. Pat. No. 364,623 to Beidler disclosed a medicine package for tablets or powders which comprised a card having perforations to receive and hold tablets "in connection with suitable covers". In this patent it is pointed out that the inventor prefers to arrange the cards or sheets in the form of a book with fly leaves interposed between the cards to prevent adhesion of the articles and to receive printed or written instructions for their administration.

Other containers for medications are disclosed in the patents to Lavigne, U.S. Pat. No. 1,453,015; Kipper U.S. Pat. No. 1,900,606; Johnson, U.S. Pat. No. 1,984,351; Mosby, U.S. Pat. No. 2,049,921; Berg, U.S. Pat. No. 2,057,180; Kidwell, U.S. Pat. No. 2,965,222; Greif et al, U.S. Pat. No. 3,305,077; and Meyers, U.S. Pat. No. 3,347,358. In some of these patents, for example, those to Meyers, Kidwell, and Greif, there is provided on the container package or sheets certain information relating to the administration of the medication.

In the more recently issued patent to Yannuzzi, U.S. Pat. No. 3,402,808, an elaborate wrist band device or locket is disclosed which device comprises an alarm, a recepticle for a medication, and a further recepticle compartment for medical information concerning the patient.

In addition to the Yannuzzi, other patents have disclosed medical history packet folders for personal medical information identification cards. Thus, for example, see the Canadian Patent No. 702,905, issued Feb. 2, 1965; and the Australian Patent No. 282,784 lodged Dec. 12, 1963.

Despite the existence for many years of all of these various prior art devices, none of them, either alone or in combination, has been developed to provide personal patient information with an emergency medication dosage in a form which could be readily and conviently carried by a patient in his pocket or around his neck at all times. Apparently the prior art devices have either been difficult and costly to fabricate, failed to have provided the needed information, or failed adequately to provide the necessary medication —this, despite the great need for some such informational package device, particularly by diabetics, who number in the millions in the United States alone.

SUMMARY OF THE PRESENT INVENTION

By the present invention the patient, such as a diabetic, may be provided with an inexpensive medical identification and information card which can readily be viewed from the outside and which with framing, fitting within the fold of the card may contain a packet of sugar to be administered to the diabetic in time of need in accordance with instructions clearly printed and visible on the outside of the card. The entire card and sugar medication package is contained in an envelope, preferably of transparent plastic, which thus may either be carried conveniently in the patient's pocket or hung around his or her neck by a cord or chain. The medical identification and information concerning the patient and the administration of the sucrose medication is clearly printed on the outside of the card and is visible through the plastic jacket, or if the jacket should not be transparent, at least some information might be printed on the outside of the jacket itself. When the card is withdrawn from the plastic jacket, it may be readily opened by a slight unfolding thereby to eject the medication, such as the packet of sugar, which may then be immediately administered by the diabetic himself or by any person attempting to assist the diabetic, in accordance with the instructions printed on the outside of the card.

This packet may be continuously reused simply by replacing the packet of sugar after it may have been dispensed to the diabetic at the time of his emergency.

There is printed on the outside of the card, clearly visible through the plastic jacket in large block type, information to flag the attention of any person who comes to the assistance of the diabetic as, for example, the words "I have diabetes" or "If I need help".

Medical information packages of this kind with the necessary medication may be produced at a minimum of expense. Desirably, the medical information to be placed on the card should be furnished by the patient's doctor.

Because of the inexpensive nature of the item, its practicality and usefulness, it is believed that medical information packages of this kind should have widespread appeal to patients and will be extensively adopted by most diabetics.

BRIEF DESCRIPTION OF THE DRAWINGS

In the accompanying drawings,

FIG. 1 is a perspective view of the informational card package shown from one side thereof;

FIG. 2 is a perspective view of the other side of the package in FIG. 1 showing the card partly withdrawn from the envelope;

FIG. 3 is a perspective view of the card completely withdrawn from the envelope and partially unfolded to disclose the internal framing and sugar package;

FIG. 4 is a plan view of the outside of the medical information card completely unfolded and laid flat;

FIG. 5 is similar to FIG. 3, but disclosing a different type of medication contained within the framing;

FIG. 6 is an alternative embodiment showing the package adapted for hanging from the neck of the patient; and FIG. 7 is a further alternative embodiment of the invention.

DESCRIPTION OF THE PREFERRED EMBODIMENT

Referring to FIGS. 1 through 4 inclusive of the drawings which illustrate an embodiment of the invention particularly adapted for a diabetic patient, a plastic envelope or jacket 10, open at one end 12, and fabricated of transparent material, houses a card 14 slideably insertable into and out of the envelope or jacket 10, as best shown in FIG. 4. The card 14 is constructed so that it may be folded along two lines 16 and 18 thereby to leave an area 20 which, when the two card portions 14a and 14a re so folded about the lines 16 and 18 respectively and brought parallel to each other, is disposed substantially normally to both the card portions 14a and 14b. On the outside of the card portion of the card 14a may be printed or otherwise provided information concerning the patient and particularly calling attention to the viewer the fact that the patient carrying the card is a diabetic. Specific directions may also be provided on the outside of the card 14a and further information as to the identification of the patient who is carrying the card and other medical data concerning the patient, may be placed on the outside of the other portion of the card 14b.

Disposed within folded portions 14a and 14b of the card 14, and having outside linear dimensions corresponding with those of each said card portion 14a and 14b, said two portions are brought into registry, is a frame 22, having a thickness substantially equal to the height of the area 20. The frame 22 is configured to define a recess 24, which preferably is rectangular and is of such size as conveniently to receive a conventional package of sugar 26 such as packages of the type often found on the tables in restaurants.

In use after all patient information has been placed on the outsides of the two card portions 14a and 14b and the frame 22 is laid onto the inside of portion 14b in register therewith, the package of sugar 26 may be deposited within the recess 24, defined by the frame 22, and the other portion 14a is brought down over the frame 22 to coincide therewith. One lateral edge 22a of the frame 22 in this arrangement will then be in abuttment with the inner surface of the area 20. The thus-assembled several elements 26, 22, and 14, as a complete package, may then be slipped into the transparent envelope or jacket 10. Desirably, one side of this jacket 12a will extend for the full length of the card 14 to protect the edge 14c which is opposite that end 14d inserted into the transparent plastic jacket or envelope 10. The other side 12b of the latter, however, may be slightly shortened and provided with a centrally disposed arcuate cut-out 12c to enable a person to place a thumb or other finger on the card 14 to enable it to be withdrawn from the jacket 10. A directional marker 28 may be printed on the outside of the card portion 14b clearly to indicate to a person seeing the card how the card may be quickly withdrawn from the jacket 10.

In the embodiment of the invention shown in FIG. 6, the one edge 12a may be provided with a reinforced arcuate projection 30 which defines an orifice 32 through which may be passed a cord or chain 34 extending around the wearer's neck.

In the embodiment of the invention shown in FIG. 5, the recess 24' defined by the frame 22' may receive a package 36 of medication tablets 38. The card thus could be used to provide emergency information and medication for patients other than diabetics who may need some such treatment.

In the further embodiment of the invention illustrated in FIG. 7, the jacket or envelope 10' may be made of a suitable paper or cardboard on which there is first printed in block type on at least one side, and preferably on both sides, some legend 36, which might read: "I AM A DIABETIC. IN THE EVENT OF AN ATTACK, PLEASE REMOVE ENCLOSED PACKET AND FOLLOW INSTRUCTIONS ON CARD".

From the foregoing, it may be seen that the present invention provides a compact, well protected identification and medical information card, together with a protected emergency supply of necessary medication which, in the case of diabetics, may comprise a conventional package of sugar. This card package combination may be fabricated, printed up and put together at such a low cost that one such card may easily be purchased and maintained by any person who needs one whatever his or her financial standing. Whenever the emergency supply of medication, such as sugar may be used up, it is a simple matter to replace the package 26 within the recess 24 and to reassemble the entire card package within the protecting plastic jacket or envelope 10.

I claim:

1. A medical identification, information, and emergency medication packet adapted for carrying or wearing by patient, said packet comprising:
   a. an envelope, open at one end and closed at its other three sides;
   b. a package insertable in said envelope, said package including
      i. a cover card of rectangular configuration said card being foldable to divide the card into two portions, one portion, upon folding, being superimposed on the other portion;
      ii. a frame of rectangular configuration conforming to the size and shape of the two card portions, said frame having an internal wall defining a recess; and
      iii. a medication package configured to fit into said recess and between the card portions when the card is folded to effect such superimposition, thereof, one upon the other;
   whereby said medication package may be completely enclosed between said two card halves and the internal wall of the frame defining said recess, said card portions having at least some of the patient's identification and medical information placed thereon and at least some notification of the patient's condition being visible from outside the envelope, so that in the event that the patient may become ill through an attack, such as one commonly experienced by diabetics or those suffering from other illnesses, any other person who may attempt to assist the patient upon seeing the packet in or upon the pocket and observing the notice visible thereon, may, upon withdrawing and examining the cover card, secure necessary instructions for relieving the patient and be provided with emergency medication to be administered to the patient in accordance with such instructions.

2. The packet as described in claim 1 wherein the envelope is formed of a transparent plastic and all notice and instructions are printed on the outside of the cover card when folded so as to be visible through envelope.

3. The packet as defined in claim 1 wherein the two card portions when folded to superimpose one upon the other are provided with an intermediate joining portion having a predetermined height and the vertical height of the frame corresponds substantially to said predetermined height.

4. The packet as defined in claim 1 wherein one side of the envelope extends further at its open end than the other side.

5. The packet as defined in claim 4 wherein said extended side is provided with an extension portion which is reinforced and is orificed to permit a cord or chain to pass therethrough.

6. The packet as defined in claim 1 wherein one side of the envelope is arcuately recessed from its open end better to enable the card to be withdrawn from the envelope.

* * * * *